United States Patent [19]
Bouricius et al.

[11] Patent Number: 5,960,089
[45] Date of Patent: Sep. 28, 1999

[54] ULTRASOUND BELL ATTACHMENT FOR STETHOSCOPE

[75] Inventors: Daniel Drill Bouricius, Boulder; Dennis Ray Newman, Golden, both of Colo.

[73] Assignee: Nicolet Vascular, Inc., Golden, Colo.

[21] Appl. No.: 08/745,406

[22] Filed: Nov. 8, 1996

[51] Int. Cl.⁶ .................................................... A61B 7/04
[52] U.S. Cl. ............................................................ 381/67
[58] Field of Search .............................. 381/67; 181/131, 181/136, 126

[56] References Cited

U.S. PATENT DOCUMENTS

| | | |
|---|---|---|
| 3,247,324 | 4/1966 | Cefaley et al. . |
| 4,618,986 | 10/1986 | Hower . |
| 4,783,813 | 11/1988 | Kempka . |
| 4,928,786 | 5/1990 | Allen ........................................ 181/131 |
| 5,347,583 | 9/1994 | Dieken ...................................... 381/67 |
| 5,498,841 | 3/1996 | Allen ........................................ 181/131 |

OTHER PUBLICATIONS

Brochure titled "Pocketful of Whoosh–Whoosh", MedaSonics, Fremont, CA 94538, dated 1995.
Brochure titled "The Harvey Elite Stethoscope", Welch Allyn Tycos, Tycos Instruments, Inc., Arden, NC 28704.
Exhibit 1: Copy of publication titled "Doplette", Imex Medical Systems, Inc.
Exhibit 2: Copy of publication titled "Mascot™", Imex Medical Systems, Inc.

*Primary Examiner*—Minsun Oh Harvey
*Attorney, Agent, or Firm*—Chrisman, Bynum & Johnson; Scott B. Allison

[57] ABSTRACT

An ultrasound bell for attachment to an acoustic stethoscope includes threads that mate with threads located on the turret of the acoustic stethoscope. The ultrasound bell includes an ultrasound transmitter for emitting ultrasound acoustic waves or signals and an ultrasound detector for receiving reflected ultrasound acoustic waves and converting the reflected ultrasound acoustic waves into electric signals. Electronic circuitry within the ultrasound bell converts the electric signals created by the ultrasound detector into sound waves emitted by a speaker. The speaker is acoustically coupled to the turret of the acoustic stethoscope such that an airtight acoustic wave pathway is formed between the ultrasound bell and the turret of the stethoscope.

30 Claims, 4 Drawing Sheets

ULTRASOUND BELL ATTACHMENT FOR STETHOSCOPE

BACKGROUND OF THE INVENTION

1. Field of the Invention

This invention is directed generally to a medical diagnostic device that use Doppler ultrasound for obstetrical and vascular monitoring applications, and more specifically, to a doppler ultrasound bell that is attachable to an acoustic stethoscope.

2. Description of the Prior Art

Doctors, paramedics, nurses, etc. have used stethoscopes for years to transmit sounds such as, for example, heart sounds, via a column of air from a patient being examined to the human ear. Stethoscopes are used to evaluate the cardiac and respiratory systems by allowing the user to distinguish the sounds that the beating heart generates, as well as the sounds of gas exchange in the lungs. The quality of the sounds denotes whether the organ in the patient being examined is healthy or unhealthy. A stethoscope can also be used to measure arterial blood pressure in a patient's arm or leg.

A conventional acoustic stethoscope generally includes two flexible rubber tubes connected to eartips or ear pieces at one end and a chest piece at the other end. The chest piece usually includes turret attached to at least one bell shaped cone that transmits low-pitched sounds via a column of air to the eartips or a diaphragm that transmits high-pitched sounds via a column of air to the eartips. The turret on a chestpiece will often include threads so that acoustic bells or diaphragms of different sizes and shapes can be attached to and removed from the stethoscope, thereby increasing the versatility of the stethoscope. In addition, many of the turrets on many conventional acoustic stethoscopes are capable of simultaneous attachment to multiple diaphragms or bells, further increasing the versatility of the acoustic stethoscope. Furthermore, electronic stethoscopes have been developed which amplify the sounds generated through the bell or diaphragm so as to improve the diagnostic capabilities of the user. For example, U.S. Pat. No. 3,247,324 issued to Cefaly et al., U.S. Pat. No. 4,618,986 issued to Hower; and U.S. Pat. No. 4,783,813 issued to Kempka disclose electronic stethoscopes.

In addition to stethoscopes, the diagnostic capabilities of the medical profession have increased significantly throughout the years. Two such advancements have been in the use of Doppler ultrasound based devices to detect and measure vascular and cardial blood flow direction and rate, to detect and measure fetal heart rate, and for numerous other diagnostic applications.

The basic Doppler effect for sound is well-known. When a source of sound and a receiver of the sound move in relation to each other, the pitch or frequency of the sound perceived or detected at the receiver is different from the pitch or frequency of the source. If they are moving toward each other, the perceived or received pitch or frequency of the sound is higher than the source sound. The classic example is standing near a railroad track as a train blowing its whistle passes. As the train approaches, the perceived whistle sound is a high pitch, which then changes abruptly to a lower pitch as the train passes and goes away from the listener.

Ultrasound is simply sound that has a higher pitch or frequency than the hearing capability of a normal human ear, which is about twenty kilohertz (20 KHz). The Doppler effect for ultrasound is the same as for audible sound, but, since ultrasound is at a pitch or frequency beyond the range of human ears, electronic equipment is used to detect it.

The Doppler effect is also produced in echoes, when sound or ultrasound is reflected by, or bounced off, a moving object. Thus, sound or ultrasound can be produced and projected by a speaker device or ultrasound sender, and, if it reflects or bounces off an object or target, the echo or return sound can be received and detected. If the ultrasound source, target object, and echo receiver are all stationary, the pitch or frequency of the echo ultrasound will be the same as the source ultrasound. However, if the target object is moving toward the receiver of the ultrasound echo, the ultrasound echo received and detected will have a higher pitch than if the target object was moving away from the receiver. The speed or velocity at which the target object is moving toward or away from the receiver determines the pitch or frequency of the echo received. Also, a fluid, such as blood, also reflects ultrasound waves, and the velocity or rate of blood flow determines the frequency of the echoed ultrasound waves. Thus, detecting frequencies of the echoed ultrasound waves can be used to measure direction and rate of blood flow. This Doppler effect in echoed ultrasound is the principle that is typically utilized in ultrasound medical diagnostic devices, where ultrasound signals having frequencies in the range between one (1) megahertz (MHz) and twenty (20) MHz are often used.

In medical diagnostic devices using Doppler ultrasound, the source of the ultrasound and the receiver of the ultrasound are usually transducers mounted in a hand-held probe. The probe is held relatively stationary with respect to a target object being detected or measured. Some slow movement and positioning of the probe by the physician or technician can be accommodated for detecting, if it is substantially slower than the motion of the target object. However, where accurate measurements are needed, the probe should be held quite stationary. An ultrasound wave stream is transmitted by the transducer in the probe in the direction of the target object to be detected or measured, and after the reflected ultrasound wave is received, an electric signal is created by a transducer that has both a frequency and an amplitude that corresponds to the frequency and amplitude of the reflected ultrasound waves. For example, in obstetrical applications, such as detecting or measuring fetal heart rate, the ultrasound waves from the probe are directed so as to intercept the blood flowing in a beating fetal heart. In vascular applications, the ultrasound waves from the probe are directed to intercept blood moving and circulating in a vein or artery to detect or measure blood flow and direction. In both situations, the directed signal from the probe is reflected by the flowing blood, which creates Doppler shifts from the frequency of the ultrasound by the probe to the frequencies of the echoed ultrasound reflected from the flowing blood. The reflected ultrasound waves from the flowing blood is detected by a transducer in the probe, which converts ultrasound waves energy to electric signals. The Doppler frequency shift between the directed ultrasound and the reflected ultrasound waves returned from the flowing blood varies proportionally with the instantaneous velocity of the flowing blood. If the blood is flowing away from the directed ultrasound from the probe, the reflected ultrasound waves will lower frequencies than the directed ultrasound. If the blood is flowing toward the directed ultrasound from the probe, the reflected ultrasound waves will have higher frequencies than the directed ultrasound. Of course, if the moving target is not moving in relation to the directed ultrasound from the probe, the reflected ultrasound wave will have the same frequency as the directed ultrasound.

Doppler ultrasound techniques for medical diagnostic purposes are well known in the art. For example, see Peter Atkinson & John Woodcock, DOPPLER ULTRASOUND AND ITS USE IN CLINICAL MEASUREMENT, published by Academic Press of New York City (1982); Matthew Hussey, BASIC PHYSICS AND TECHNOLOGY OF MEDICAL DIAGNOSTIC UULTRASOUND, published by Elsevier of New York City (1985); and Peter Fish, PHYSICS AND INSTRUMENTATION OF DIAGNOSTIC MEDICAL ULTRASOUND, published by John Wiley & Sons of New York City (1990). See also, U.S. Pat. No. 4,276,491 issued to Daniel; U.S. Pat. No. 4,807,636 issued to Skidmore et al.; U.S. Pat. No. 4,850,364 issued to Leavitt; and U.S. Pat. No. 5,394,878 issued to Frazin all of which show medical devices using Doppler ultrasound techniques. Furthermore, Doppler ultrasound has become a popular method of medical diagnosis because it is non-invasive, painless, creates little or no side effects, and is relatively inexpensive. Finally, ultrasound frequencies are often used in medical diagnostic applications because they reflect well from the boundaries between different organs and blood cells without utilizing potentially harmful ionizing radiation.

In many medical diagnostic applications using Doppler ultrasound, the transmitter of the directed signal is placed directly against the human skin. For example, when measuring fetal heart rate, the transmitter is placed on the midline of the abdomen and aimed downward toward the pubic bone. When measuring vascular flow, the transmitter is placed directly over the underlying vessel. The direct contact between the transmitter and the human skin is necessary to reduce reflections of the directed ultrasound and the reflected ultrasound echo caused by the skin, and ultrasound does not propagate well in air at the frequencies used in these applications. To facilitate ease of use and manual manipulation of diagnostic devices using Doppler ultrasound, as described above, it is desirable to have a device that is small, portable, and battery operated, since the probe must often be placed directly next to the skin of the patient being tested.

The use of Doppler ultrasound has gained wide acceptance in the medical profession. Furthermore, ultrasound probes that are attachable to the flexible rubber ear tubes that are a part of conventional stethoscopes are known in the art. For example, the Doplette™ doppler device manufactured by Imex Medical Systems, Inc., of Golden, Colo., allows an ultrasound transmitter and receiver to be removably connected to the ear tubes from a conventional acoustic stethoscope. The Doplette™ doppler device, however, requires that the chestpiece and turret of the stethoscope be removed so that the Doplette™ doppler device can be attached directly to the flexible hose or tube. The Mascot™ system, also manufactured by Imex Medical Systems, allows a doppler ultrasound probe to be interchanged with an electronic stethoscope probe. The Mascot™ system, however, functions as an electronic stethoscope and requires that the ultrasound probe be removed when the stethoscope probe is being used, and vice-versa.

Despite the well developed state of the art in both stethoscope and ultrasound devices, there remains a need for an ultrasound probe or bell to be attachable to the turret of a conventional acoustic stethoscope and, more specifically, a need for the capability of simultaneously attaching an ultrasound bell and an acoustic bell or diaphragm to a conventional acoustic stethoscope.

SUMMARY OF THE INVENTION

Accordingly, it is a general object of this invention to provide an ultrasound bell connected to a conventional acoustic stethoscope.

It is another general object of this invention to provide an ultrasound bell that is removably attached to an acoustic stethoscope.

It is a specific object of this invention to provide an ultrasound bell that can be connected to an acoustic bell on an acoustic stethoscope.

Additional objects, advantages, and novel features of the invention shall be set forth in part in the description that follows, and in part will become apparent to those skilled in the art upon examination of the following or may be learned by the practice of the invention. The objects and the advantages may be realized and attained by means of the instrumentalities and in combinations particularly pointed out in the appended claims.

To achieve the foregoing and other objects and in accordance with the purposes of the present invention, as embodied and broadly described herein, the ultrasound bell attachment for an acoustic stethoscope includes a bell having threads that removably mate with threads on the turret of the acoustic stethoscope; electronic circuitry and power for transmitting ultrasound acoustic waves or signals, receiving reflected ultrasound acoustic waves or signals, and converting the received ultrasound acoustic waves or signals into an electric signal; a speaker driven by the electric signal that creates an audible sound wave; and a coupler that couples the speaker to the turret such that an acoustic pathway is created between the speaker and the turret and audible sound waves are transmitted from the speaker into the turret of the acoustic stethoscope. In an alternative embodiment, the ultrasound bell is attached to the rim of an acoustic bell.

BRIEF DESCRIPTION OF THE DRAWINGS

The accompanying drawings, which are incorporated in and form a part of the specification, illustrate the preferred embodiments of the present invention, and together with the descriptions serve to explain the principles of the invention. In the Drawings.

DETAILED DESCRIPTION OF THE PREFERRED EMBODIMENTS

Figure 1:
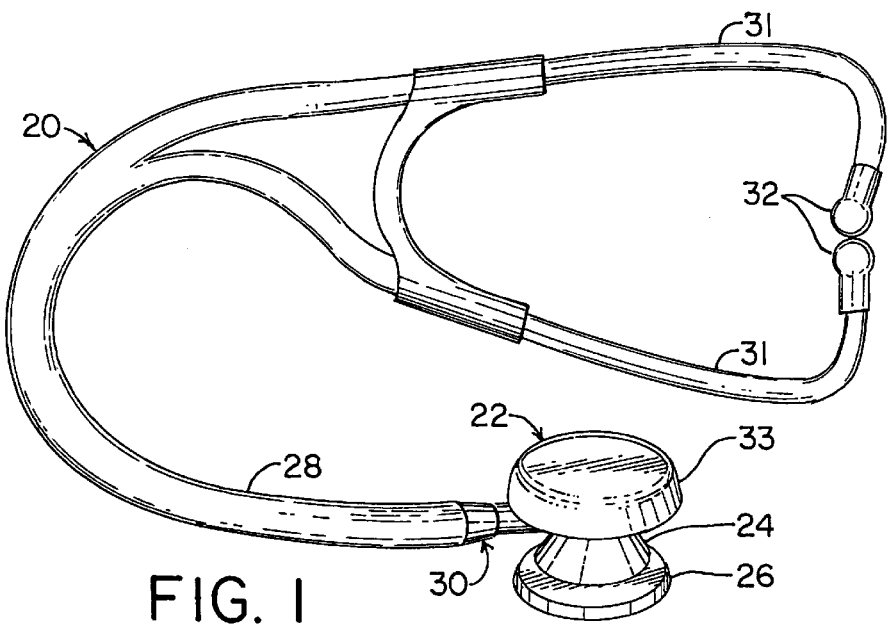
FIG. 1 is an isometric view of the stethoscope of the present invention, including an acoustic bell and an ultrasound bell attached to stethoscope tubing and earpieces.

The stethoscope 20 having the ultrasound bell 22 attachment of the present invention shown in FIG. 1 includes a removable ultrasound bell 22 attached to a turret or chestpiece 24 for transmitting ultrasound acoustic waves or signals into a patient P, receiving reflected ultrasound acoustic waves from a patient P, and using an electric signal that is a function of the transmitted and received ultrasound waves to generate an audible sound wave, an optional removable acoustic bell 26 attached to the opposite side of the turret 24 from the ultrasound bell 22 for listening to sounds produced by the patient P, the flexible acoustical conduit or tubing 28 which is attached to the turret 24 via the turret coupler 30 for transmitting or channeling the sound waves produced by the ultrasound bell 22 or the acoustic bell 26 to the binaurals 31 and the eartips or earpieces 32.

A significant feature of the stethoscope of the present invention includes the ultrasound bell 22 which is attachable to, and removable from, a conventional stethoscope turret or chestpiece 24 on a standard stethoscope. The ultrasound bell 22 allows the operator to use Doppler ultrasound to detect and measure vascular and cardial blood flow direction and rate in the patient P, to detect and measure fetal heart rate, for numerous other ultrasound diagnostic and monitoring applications, and for measuring physical phenomena in the patient's P body, while the ultrasound bell 22 is connected to a conventional stethoscope familiar to most doctors, nurses, etc. The use of Doppler ultrasound for medical diagnostic and monitoring purposes is well know to persons having ordinary skill in this art and need not be discussed any further for purposes of the ultrasound bell 22 of the present invention.

The stethoscope turret 24 may also simultaneously provide for the permanent or removable attachment of a conventional acoustic bell 26 or conventional diaphragm (not shown) as well, thereby allowing a doctor, nurse, paramedic, etc. to easily and quickly change as desired between using an ultrasound bell 22 or acoustic bell 26 to listen to a patient P. In a first embodiment, the ultrasound bell 22 can be used with a standard stethoscope simply by replacing an acoustic bell with the ultrasound bell 22. In a second embodiment, the ultrasound bell 22 can be attached to a standard stethoscope by attaching and acoustically connecting the ultrasound bell 22 to a standard acoustic bell on the stethoscope turret 24. Both embodiments will be discussed in more detail below. In general, the ultrasound bell 22 includes a housing 33 in which the components of the ultrasound bell 22 are preferably positioned, as will be discussed in more detail below. The housing 33 can be made of plastic, metal, or other suitable material or combinations of materials.

A significant advantage provided by the ultrasound bell 22 of the present invention is that the ultrasound bell 22 can be attached to a conventional acoustic stethoscope and, more specifically, to a conventional stethoscope turret or chestpiece 24. A conventional acoustic stethoscope includes a turret 24 that is either permanently attached to an acoustic bell or diaphragm, such as the acoustic bell 26, or includes the threads 34 which allow bells and diaphragms of different sizes to be attached to the turret 24. Positioned within the turret 24 is the spindle 36 which forms part of the acoustical turret coupler 30 between the turret 24 and the flexible acoustic conduit or tubing 28. The spindle 36 includes the bore 38 so that sound waves can be channeled or transmitted from the ultrasound bell 22 or the acoustic bell 26 to the acoustic conduit or tubing 28. In most conventional stethoscopes, the bore 38 does not generally extend longitudinally all the way through the spindle 36, but instead extends to the port 39 on the spindle 36. When multiple bells or diaphragms are attached or attachable to the turret 24, the spindle 36 is preferably rotatable about the axis 40 within the turret 24 so that the port 39 on the spindle 36 can be positioned adjacent and aligned with either the turret port 42 on the acoustic bell 26 side of the turret 24 or the turret port 44 on the opposite side of the turret 24. The construction and operation of a turret for a conventional stethoscope, including the rotatable spindle, are well known to people having ordinary skill in this art, and need not be discussed any further for purposes of the ultrasound bell 22 of the present invention.

Figure 2:
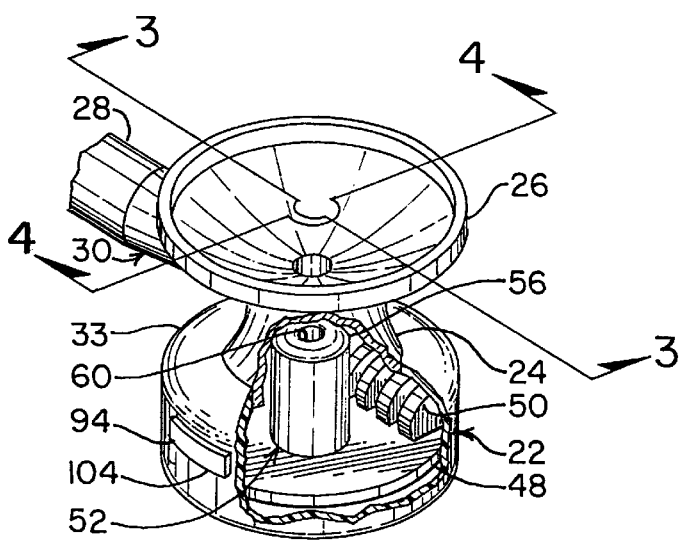
FIG. 2 is an isometric view of the acoustic bell and ultrasound bell of FIG. 1, wherein the ultrasound bell is cutaway to show the inner portion of the ultrasound bell which includes a battery, a printed circuit board, and an acoustic coupler.
Figure 3:
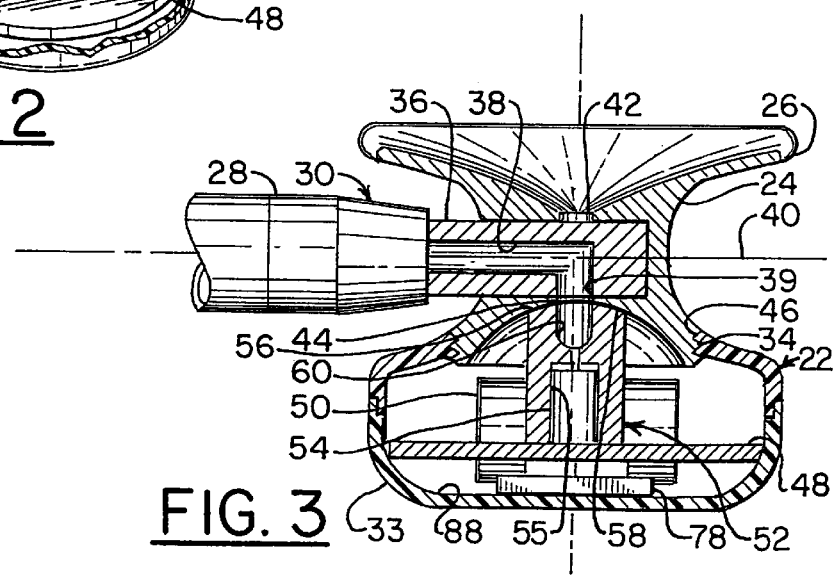
FIG. 3 is an elevation view of the isometric bell and the ultrasound bell of FIG. 2, taken along the line 3—3 of FIG. 2.

Now referring to FIGS. 2–4, the preferred structure of the ultrasound bell 22 will now be discussed in more detail. The ultrasound bell 22 preferably includes the threads 46 on the housing 33 so that the ultrasound bell 22 can be screwed onto and attached to the turret 24 which includes the threads 34 that mate with the threads 46 on the housing 33 of the ultrasound bell 22. Located within the housing 33 of the ultrasound bell 22 is the printed circuit board 48 upon which the components (not shown) in the electronic circuitry of the ultrasound bell 22 are located or attached. The printed circuit board 48 can be glued, bonded, or otherwise adhesively attached to the housing 33 or attached to the housing 33 via rivets, screws, clips, etc. (not shown). For purposes of ease of explanation of the present invention and clarity of the Figures, the components in the electronic circuitry of the ultrasound bell 22, which are generally positioned on the printed circuit board 48 or otherwise in the housing 33, are not shown in the Figures. A battery or battery pack 50 is located within the ultrasound bell 22 to provide electric power to the electronic circuitry located on the printed circuit board 48 in the ultrasound bell 22. While the first embodiment of the ultrasound bell 22 preferably includes the threads 46 on the housing 33 for attaching the ultrasound bell 22 to the turret 24, the ultrasound bell 22 can also be adhesively attached or bonded to the turret 24, particularly if the turret 24 and the housing 33 do not include the threads 34, 46, respectively. The adhesive attachment or bond of the ultrasound bell 22 to the turret 24 can also be used when the attachment of the ultrasound bell 22 to the turret 24 is to be permanent.

A significant feature of the ultrasound bell 22 is the acoustic coupler 52 which surrounds the transducer or converter 54. The transducer 54, which includes a speaker 55, converts electrical signals generated by electronic circuitry on the printed circuit board 48 into sound waves which are emitted by the speaker 55 in a direction generally directed upward toward the turret port 44 and propagate through the hollow bore or duct 60 in the acoustic coupler 52 to the turret port 44 on the turret 24, as will be discussed in more detail below. The transducer 54 can be, for example, a BK 1600 Subminiature Transducer manufactured by Knowles Electronics, Inc., of Franklin Park, Ill., although many other kinds of transducers or speakers will work for the purposes of the present invention. The wide range of possible transducers having different shapes and audio frequencies enables ultrasound bells to be designed for many specific purposes such as, for example, locating arteries prior to catheterization. During operation and use of the ultrasound bell 22, ultrasound waves or signals are transmitted out of the ultrasound bell 22 and into a patient P which causes ultrasound waves or signals to reflected back toward the ultrasound bell 22 to be detected. The transmitted ultrasound waves and the reflected ultrasound waves are used by the ultrasound bell 22 to create the electric signal that drives the transducer 54 containing the speaker 55 so that sound waves are emitted by the speaker 55, as will be discussed in more detail below.

The acoustic coupler 52 preferably forms a tight seal around the transducer 54, particularly the speaker 55 on the transducer 54, and preferably extends from the printed circuit board 48 upward to the turret port 44 so that the surface 56 of the acoustic coupler 52 forms a airtight and possibly hermetic seal with the surface 58 of the turret 24 and so that the turret port 44 is aligned with the bore 60 of the acoustic coupler 52. The acoustic coupler 52 can be, but is not required to be, glued, bonded, or otherwise adhesively attached to the printed circuit board 48. In the embodiment shown in FIGS. 1–6, the surface 56 of the acoustic coupler 52 is convex so that it mates properly with and forms a tight seal with the concave surface 58 of the turret 24. Should the surface 58 of the turret 24 have a different size or shape, the surface 56 of the acoustic coupler 52 should be size and shaped according to maintain an airtight seal with the surface 58 of the turret 24.

The bore 60 in the acoustic coupler 52, the turret port 44, and the bore 38 in the spindle 36 form a continuous air channel or duct so that sound waves produced by the speaker 55 of the transducer 54 will be directed and transmitted from the ultrasound bell 22 to the turret 24, through the turret coupler 30, the acoustical conduit 28, and the binaurals 31 to be heard by the user of the stethoscope 20 through the eartips 32. An airtight seal between the transducer 54, specifically the speaker 55, and the acoustic coupler 52, and between the acoustic coupler 52 and the turret port 44, prevents the pressure created by the acoustic sounds waves generated from the speaker 55 on the transducer 54 from dissipating, thereby insuring adequate acoustic pressure in the acoustical conduit 28 so that sound waves will propagate through the acoustical conduit 28 without significant attenuation. The ultrasound bell 22 may also include other sealing features, such as o-rings, seals, etc. (not shown) to improve the seal between the bore 60 in the acoustic coupler 52 and the turret port 44 and the seal between the surface 56 of the acoustic coupler 52 and the turret port 44.

The size and shape of the acoustic coupler 52 can vary, depending on the size and shape of the transducer 54 and the speaker 55, so long as an airtight seal is created between the speaker 55 and the turret port 44. The acoustic coupler 52 can be made of rubber, plastic, elastomeric material, or other suitable material. The transducer 54 is preferably positioned on the center of the printed circuit board 48 so that the speaker 55 is aligned and coaxial with the turret port 44 and so that the speaker 55 emits sound waves in a direction generally toward the turret port 44. In other words, the transducer 54, the speaker 55, and the acoustic coupler 52 are preferably positioned coaxial with the central axis 61 of the housing 33. In addition, positioning the speaker 55 on the printed circuit board 48 so that the speaker 55 is coaxial with the turret port 44, reduces the size of the acoustic coupler 52, reduces the length of the bore 60 in the acoustic coupler 52, and simplifies the shape of the acoustic coupler 52. The present invention does not require, however, that the transducer 54, speaker 55, or acoustic coupler 52 be coaxial with the turret port 44. In fact, the transducer 53 and speaker 55 can be positioned almost anywhere on the printed circuit board 48 or within the ultrasound bell 22, so long as the acoustic coupler 52, which may have a different size and shape than shown in FIGS. 2–6, forms an airtight channel or duct between the transducer 54, specifically the speaker 55, and the turret port 44.

Figure 6:
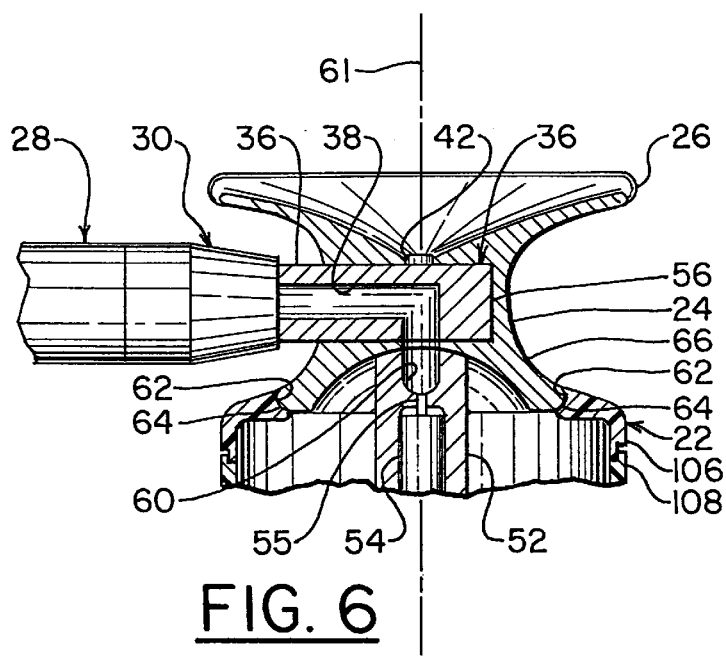
FIG. 6 is an elevation view of the acoustic bell of FIG. 2 and a second embodiment of the ultrasound bell of FIG. 2.

In an alternative embodiment shown in FIG. 6, the housing 33 of the ultrasound bell 22 does not include the threads 46. Instead, the ultrasound bell 22 includes the concave-shaped rim surface 62 which snaps over and mates with the convex-shaped rim surface 64 of a standard acoustic bell 66, thereby allowing the ultrasound bell 22 to "piggyback" onto and attach to the conventional acoustic bell 66. In the second embodiment of the ultrasound bell 22, the turret 24 may not include any threads, thereby preventing the acoustic bells 26 and 66 from being removed from the turret 24 and making it impossible for the ultrasound bell 22 of the first embodiment to be attached to the turret 24. The concave surfaces 62 on the housing 33 of the second embodiment of the ultrasound bell 22, therefore, allow the ultrasound bell 22 to be snapped on or otherwise attached to, and removed from, an acoustic bell 66 of a conventional acoustic stethoscope, thereby increasing the versatility of the stethoscope. Other coupling mechanisms (not shown) between the ultrasound bell 22 and the turret 24 or the ultrasound bell 22 and the acoustic bell 66 are also possible, so long as an airtight seal is created between the speaker 55 on the transducer 54 and the turret port 44 to channel the sound waves emitted by the speaker 55 of the transducer 54 to the turret 24. For example, while the second embodiment of the ultrasound bell 22 preferably includes the concave shaped surface 62 on the housing 33 for attaching the ultrasound bell 22 to the acoustic bell 66, the ultrasound bell 22 can also be adhesively attached or bonded to the acoustic bell 66. The adhesive attachment or bond of the ultrasound bell 22 to the acoustic bell 66 can also be used when the attachment of the ultrasound bell 22 to the acoustic bell 66 is to be permanent.

Now referring to FIG. 7, the operation of the electronic circuitry within the ultrasound bell 22 will now be discussed in more detail. It should be noted that many designs of ultrasound circuitry are usable with the ultrasound bell 22 of the present invention and the ultrasound bell 22 should not be limited to only the electronic circuitry described herein. The RF oscillator 70 creates the frequency of the ultrasound signals transmitted by the ultrasound bell 22 and which are directed into the patient P. The frequency generated by the RF oscillator may vary depending on the application of the ultrasound bell. For example, a two (2) megahertz (MHz) or a three (3) MHz signal might be used for obstetric applications to detect fetal heartbeats. A two (2) MHz signal is best suited for detecting fetal heartbeats after the fetus is twelve weeks old and throughout labor and delivery. A three (3) MHz signal has the increased sensitivity needed for the early stages of pregnancy. A five (5) MHz or an eight (8) MHz signal might be used in vascular applications. The five (5) MHz signal is better suited for deep arterial and venous flow detection, while the eight (8) MHz signal can be used for superficial vessel measurements. The electronic circuitry in the ultrasound bell 22 can also be configured to generate pulsed ultrasound waves or signals or continuous ultrasound waves or signals.

The RF oscillator 70 provides in input signal for the driver 72 and for the mixer 74. The driver 72 functions as a class C amplifier an provides power amplification and an impedance match between the RF oscillator 72 and the ultrasound transmitter 76. The ultrasound transmitter 76 can be a piezoceramic or other suitable device such as, for example, a PZT-5A material manufactured by Morgan Matroc, Inc., of Bedford, Ohio.

Figure 4:
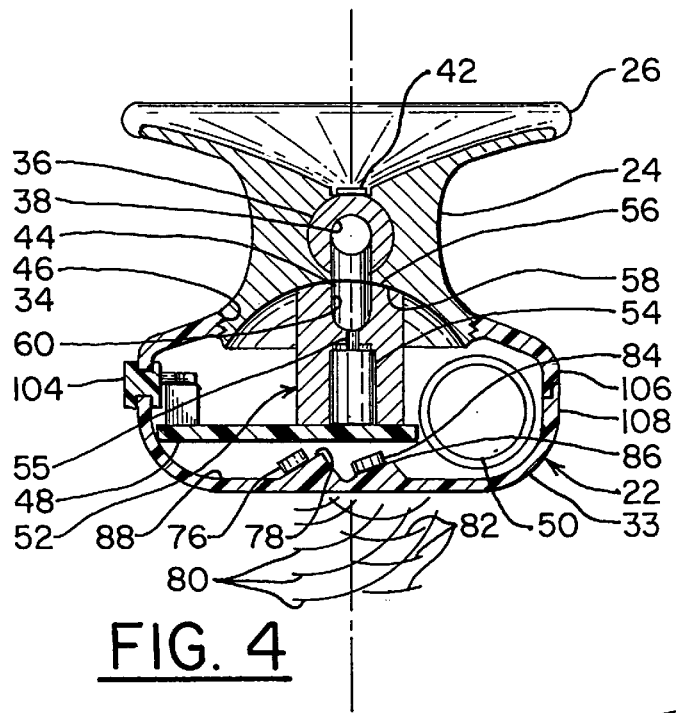
FIG. 4 is another elevation view of the isometric bell and the ultrasound bell of FIG. 2, taken along the line 4—4 of FIG. 2.
Figure 5:
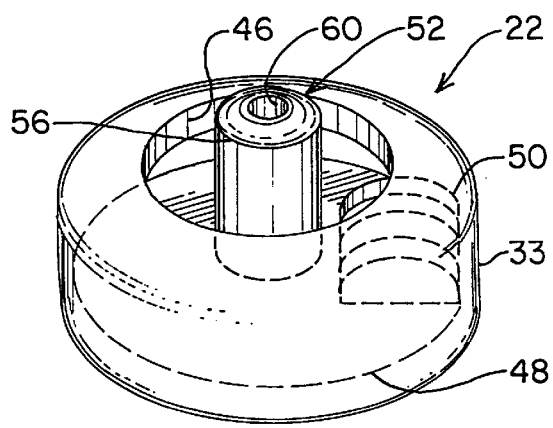
FIG. 5 is an isometric view of the ultrasound bell of FIG. 2, wherein the ultrasound bell is shown unattached to the remainder of the ultrasound stethoscope of FIG. 2.

The ultrasound transmitter 76 is preferably positioned on the interior inclined surface 78 (see FIGS. 3 and 4) of the housing so that ultrasound acoustic waves or signals at a constant frequency are emitted at an angle (i.e., in a non-perpendicular direction) outward from the ultrasound bell 22 toward the patient P, as indicated by the waves or signals 80 in FIG. 4. The acoustic waves or signals 80 that are generated and transmitted by the transmitter 76 propagate outward through the housing 33 to the patient P. The blood (not shown) flowing in the heart, artery, vein, etc. of the patient P reflects the ultrasound waves 80 transmitted from the transmitter 76 and causes a Doppler frequency shift in the reflected ultrasound waves or signals 82 (see FIG. 4) that corresponds to the velocity of flowing blood (not shown) in the patient P. The reflected ultrasound waves or signals 82 are detected by the receiver 84 that is preferably positioned on the interior inclined surface 86 on the housing 33 in the ultrasound bell 22 (see FIG. 4). Placing the transmitter 76 and the receiver 84 on the inclined surfaces 78, 86, respectively, is preferred for certain vascular applications in order to provide an angle of less than 90° between the ultrasound beam and the flowing blood. The angles between the inclined surfaces 78, 86 and the generally flat interior surface 88 of the housing 33 of the ultrasound bell 22 are preferably different so that a significant overlap of the transmitted waves 80 and the reflected waves 82 exist and so that the transmitter 76 and the receiver 84 can be placed in close proximity to each other inside the ultrasound bell 22.

The ultrasound receiver 84 detects the reflected ultrasound echo waves 82 that propagate through the housing 33 and produces an electric signal that has the same frequency as, and an amplitude proportional to, the reflected ultrasound waves 82. The output signal from the receiver 84 is the input signal to the RF preamplifier 90 which amplifies the Doppler signal prior to demodulation and can have a gain of, for example, twenty (20). The RF preamplifier 90 can use, for example, an NPN transistor $Q_5$ (see FIG. 8) configured in a common-emitter configuration. The output signal from the RF preamplifier 90 is an input signal to the mixer 74 so that the electric signal from the RF preamplifier 90 and be heterodyned or modulated (usually, but not necessary, frequency modulation) by the mixer 74 with the electric signal from the RF oscillator 70. The mixer 74 can include, for example, an NE602 Double balanced mixer IC manufactured by Philips of Sunnyvale, Calif.

In the heterodyne or modulation process in the mixer 74, the electric signal from the RF oscillator 70, which represents the frequency of the ultrasound waves 80 transmitted by the transmitter 76, is mixed with the electric signal from the RF preamplifier, which represents the frequency of the reflected ultrasound waves 82 detected by the receiver 84, to produce an electric signal that has a beat frequency equal to the difference between the frequency of the transmitted waves or signals 80 and the frequency of the reflected waves or signals 82. The beat frequency varies between zero, when there is no difference between the frequency of the transmitted waves 80 and the frequency of the reflected waves 82, to some frequency in the audible hearing range, representing the velocity of the moving target, for example, flowing blood or a beating heart, and the beat frequency is proportional to the velocity of the moving target. An audio frequency electric signal can be produced from this heterodyne beat frequency by the mixer 74 for driving the speaker 55 to produce a sound that can be heard by the user through the eartips 32. Therefore, the output electric signal from the mixer 74 is created as a function of the input signals to the mixer 74 from the RF oscillator 70 and the receiver 84.

The output signal from the mixer 74 is an input signal to the volume control 92 which is used to attenuate the Doppler audio signal from the mixer 74 for the purpose of reducing the amplitude and strength of the Doppler audio signal, and to provide the audio volume level preferred by the user. The amount of attenuation done by the volume control 92 is controlled by the user through the operation of a slide switch or potentiometer 94 (see FIGS. 2) that is accessible by the user.

The output signal from the volume control 92 is the input signal to the audio preamplifier 96 which amplifies the electric signal and provides an input signal to the signal processing and display circuitry 98 and the audio amplifier 100. The audio preamplifier can have a gain of, for example, seventy-five (75). The signal processing and display circuitry 98 is used to calculate and display the heart rate or blood velocity if desired, on the ultrasound bell 22. The audio amplifier 100 amplifies the electric signal from the audio preamplifier 96 and provides an input signal to the voltage limiter 102 which limits the maximum amplitude of the electric signal provided to the speaker 55 inside the transducer or converter 54 and, therefore, protects against excessively loud output signals. The audio amplifier 100 can have a gain of, for example, ten (10).

Power to the electronic components inside the ultrasound bell 22 is provided by the battery 50 which is connected to the electronic circuitry via the on/off switch 104 (see FIG. 2) which is accessible by the user. The battery or battery pack 50 that is used can be, for example, four D357 cells manufactured by Duracell, Inc. of Bethel, Conn. As an option, the battery or battery pack 50 can be rechargeable and/or removable to increase the versatility of the ultrasound bell 22.

Figure 7:
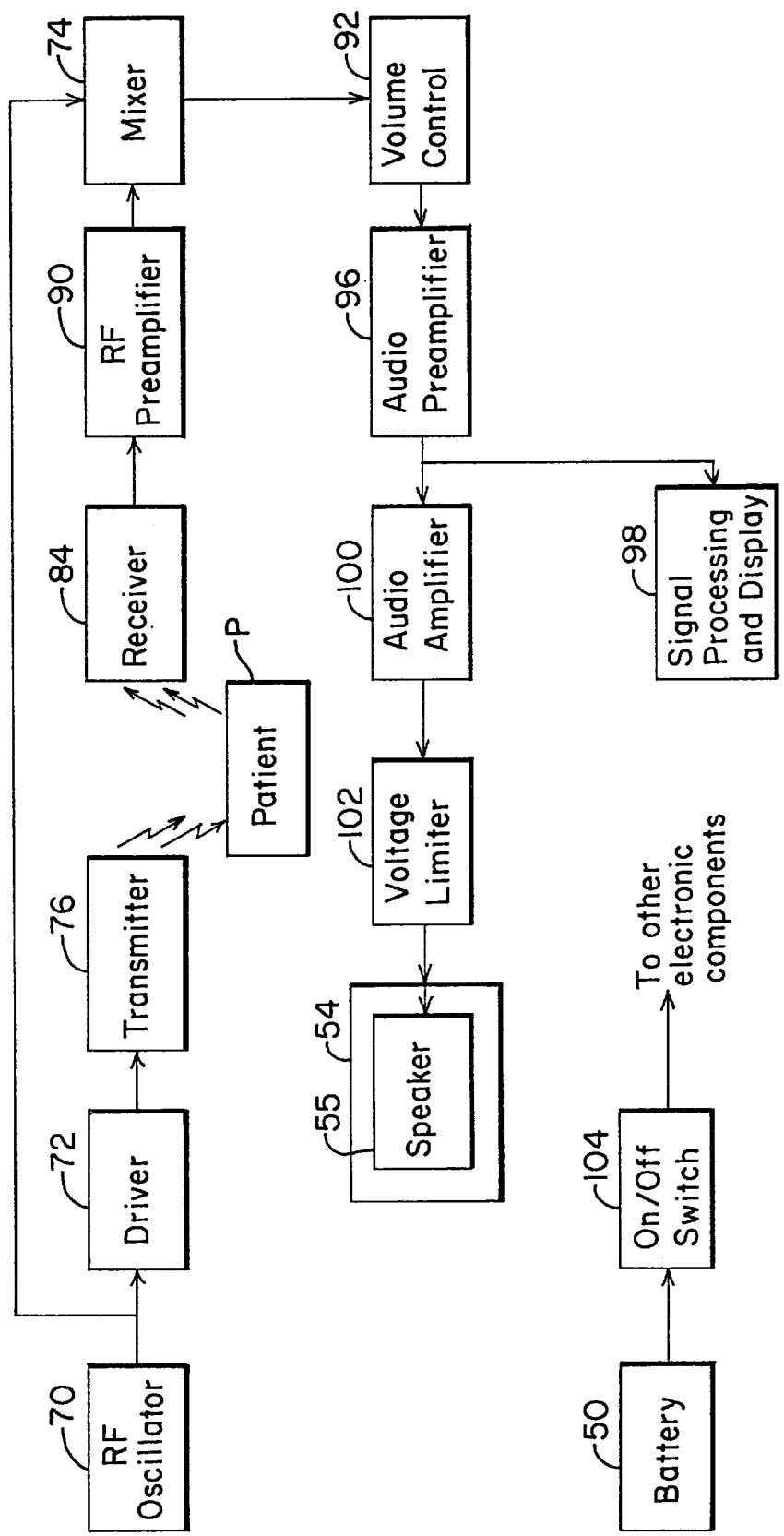
FIG. 7 is a functional block diagram of the ultrasound transmitter, receiver, doppler mixer, speaker, power supply, and other electronic circuitry used in the ultrasound stethoscope of FIG. 1.
Figure 8:
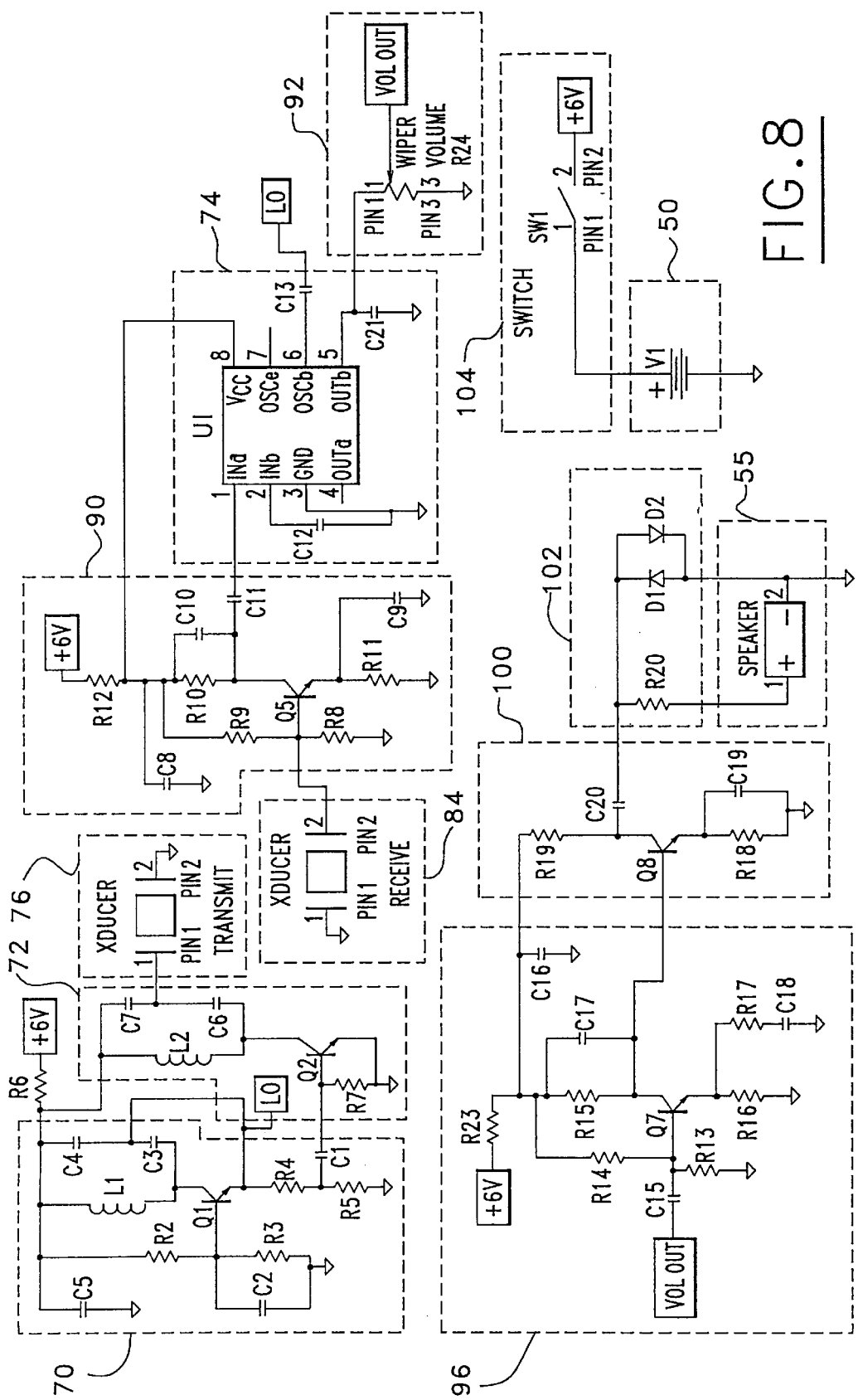
FIG. 8 is an exemplary schematic diagram of the electronic circuitry of FIG. 7.

An exemplary schematic diagram corresponding to the functional block diagram of FIG. 7 is provided in FIG. 8. Since the electronic circuitry included in the ultrasound bell 22 of the present invention is of conventional design, elaborate discussion of the complete circuit is not necessary as the schematic provided in FIG. 8 will be understood by people having ordinary skill in this art. For purposes of general explanation, but not limitation, of the ultrasound bell 22 of the present invention, however, the following information is provided.

The Doppler frequency produced in the RF oscillator 70 is created by the Colpitts oscillator formed by the transistor $Q_1$. In the example schematic diagram shown in FIG. 8, the doppler frequency of the electric signal produced by the RF oscillator 70 is 5 MHZ. The inductor $L_1$ and the capacitors $C_3$, $C_4$ form a tuned tank circuit for the purpose of creating a high impedance of 5 MHZ. A portion of the electric signal created by the tank circuit is fed back to the emitter of the transistor $Q_1$ for the purpose of positive feedback. The resistors $R_2$, $R_3$, and $R_5$ set the DC voltage bias of transistor $Q_1$. The capacitor $C_2$ establishes common-base operation of the transistor $Q_1$ by providing an AC signal bypass for the base of the transistor $Q_1$.

The transistor $Q_2$ in the driver 72 conducts over a small portion of each RF cycle of the signal received from the RF oscillator 70. The inductor $L_2$ and the capacitors $C_6$ and $C_7$ form a tank circuit for the purpose of matching impedances. The output impedance and output voltage characteristics of the tank circuit are determined in part by the ratio of the capacitance of the capacitor $C_7$ to the capacitance of the capacitor $C_6$.

The foregoing description is considered as illustrative only of the principles of the invention. Furthermore, since numerous modifications and changes will readily occur to those skilled in the art, it is not desired to limit the invention to the exact construction and process shown and described above. Accordingly, all suitable modifications and equivalents may be resorted to falling within the scope of the invention as defined by the claims which follow. For example, while the ultrasound bell 22 of the present invention is shown and discussed as being attached to a completely acoustic stethoscope, the ultrasound bell 22 can be used with many electronic stethoscopes that amplify the sounds produced by acoustic bells or diaphragms. Therefore, the ultrasound bell 22 of the present invention should not be construed as being useable with only non-electronic acoustic stethoscopes, since many electronic stethoscopes use acoustic bells and diaphragms. As another example, the housing 33 of the ultrasound bell 22 may be separable into parts 106 and 108, as best seen in FIGS. 4 and 6, so that the components of the electronic circuity, the printed circuit board 48, the battery or battery pack 50, and the interior of the ultrasound bell 22 are easily and conveniently accessible. In addition, the ultrasound bell 22 can include a wireless infrared or RF link to a remote means of audio or video display or a visual display on the outside surface of the housing 33.

The embodiments of the invention in which an exclusive property or privilege is claimed are defined as follows:

1. An attachment to a stethoscope having a turret, comprising:
    a housing attachable to the turret;
    a transmitter located in or on said housing and capable of generating at least one acoustic wave and propagating said at least one acoustic wave outward from said housing;
    a receiver located in or on said housing and capable of receiving at least one acoustic wave indicative of a modified version of said at least one acoustic wave propagated by said transmitter;
    a mixer located in or on said housing and capable of generating an electric signal representative of a function of said at least one propagated acoustic wave and said at least one received acoustic wave;
    a converter located in or on said housing and capable of generating at least one sound wave representative of said electric signal; and
    a coupler positioned between said converter such that said at least one sound wave is propagated into the turret.

2. The attachment of claim 1, wherein said converter includes a speaker and said coupler forms a hollow air duct between said speaker and the turret.

3. The attachment of claim 1, wherein said converter means includes a speaker and said coupling means forms a hollow air duct between said speaker and the turret.

4. The attachment of claim 3, wherein said hollow air duct between said speaker and the turret is substantially airtight.

5. The attachment of claim 4, wherein said hollow air duct between said speaker and the turret is completely airtight.

6. The attachment of claim 1, wherein said coupler substantially surrounds said converter.

7. The attachment of claim 1, wherein said hollow air duct between said speaker and the turret is completely airtight.

8. The attachment of claim 1, wherein said housing has a central axis and said coupler is generally symmetric about said central axis.

9. The attachment of claim 1, wherein said housing includes a wall having and said transmitter propagates said acoustic waves through said wall.

10. The attachment of claim 9, wherein said transmitter propagates said acoustic waves through said wall of said housing in a direction non-perpendicular to said wall of said housing.

11. The attachment of claim 1, wherein said housing is removably attachable to the turret.

12. An attachment to a stethoscope having an acoustic bell, comprising:
    a housing attachable to the bell;
    a transmitter located in or on said housing and capable of generating at least one acoustic wave and propagating said at least one acoustic wave outward from said housing;
    a receiver located in or on said housing and capable of receiving at least one acoustic wave indicative of a modified version of said at least one acoustic wave propagated by said transmitter;
    a mixer located in or on said housing and capable of generating an electric signal representative of a function of said at least one propagated acoustic wave and said at least one received acoustic wave;
    a converter located in or on said housing and capable of generating at least one sound wave representative of said electric signal; and
    a coupler positioned adjacent said converter and capable of propagating said at least one sound wave is into the bell.

13. The attachment of claim 12, wherein said housing is removably attachable to the bell.

14. The attachment of claim 12, wherein said housing includes a concave shaped surface matable with a convex surface of the bell.

15. An attachment to a stethoscope having a turret, comprising:
    a housing attachable to the turret;
    a transmitter located in or on said housing and capable of generating acoustic waves and propagating said acoustic waves outward from said housing;
    a receiver located in or on said housing and capable of receiving reflected acoustic waves;
    a mixer capable of generating an electric signal representative of a function of said propagated acoustic waves and said received reflected acoustic waves;
    a transducer located in said housing capable of generating sound waves representative of said electric signal; and
    a coupler positioned between said transducer and the turret capable of transmitting said sound waves to the turret.

16. An attachment to a stethoscope having a turret, comprising:
    a housing attachable to the turret;
    a transmitter in or on said housing and capable of producing at least one ultrasound signal and propagating said at least one ultrasound signal outward from said housing;
    a receiver in or on said housing and capable of receiving at least one reflected ultrasound signals;
    a mixer in or on said housing and capable of generating an electric signal representative of a modulation of said at least one propagated ultrasound signal and said at least one received ultrasound signal;
    a speaker in or on said housing and capable of producing at least one sound wave representative of said electric signal; and
    a coupler positioned between said transducer and the turret capable of transmitting said sound waves to the turret.

17. An attachment to a stethoscope having a threaded turret, comprising:
    a housing having threads matable with the threads on the turret such that said housing is attachable to the turret;
    a transmitter in or on said housing and capable of producing at least one ultrasound signal and propagating at least one ultrasound signal outward from said housing;
    a receiver in or on said housing and capable of receiving at least one ultrasound signal representing a modification of said at least one propagated ultrasound signal;
    a mixer capable of generating an electric signal representative of a modulation of said propagated at least one ultrasound signal and said received ultrasound at least one ultrasound signal;

a speaker capable of producing at least one sound wave representative of said electric signal; and a coupler positioned between said transducer and the turret capable of transmitting said at least one sound wave to the turret.

18. An attachment to a stethoscope having an acoustic bell, comprising:

a housing attachable to the bell, said housing including a transmitter capable of producing ultrasound signals and propagating ultrasound signals outward from said housing, a receiver capable of receiving reflected ultrasound signals, a mixer capable of generating an electric signal representative of a modulation of said propagated ultrasound signals and said received ultrasound signals, a speaker capable of producing sound waves representative of said electric signal, and a coupler positioned between said transducer and the bell capable of transmitting said sound waves to the bell.

19. An attachment to a stethoscope having a turret, comprising:

a housing attachable to the turret;

transmitter means in or on said housing for propagating acoustic waves outward from said housing;

receiver means in or on said housing for receiving reflected acoustic waves;

mixer means for generating an electric signal representative of a function of said propagated acoustic waves and said received acoustic waves;

a transducer located in or on said housing capable generating sound waves representative of said electric signal; and a coupler positioned between said transducer and the turret capable of transmitting said sound waves to the turret.

20. An attachment to a stethoscope having an acoustic bell, comprising:

a housing attachable to the bell;

transmitter means in or on said housing for propagating acoustic waves outward from said housing;

receiver means in or on said housing for receiving reflected acoustic waves;

mixer means in or on said housing for generating an electric signal representative of a function of said propagated acoustic waves and said received acoustic waves;

a transducer located in or on said housing capable generating sound waves representative of said electric signal; and a coupler positioned between said transducer and the bell capable of transmitting said sound waves to the bell.

21. An attachment to a stethoscope having a turret with a turret port, comprising:

a housing attachable to the turret;

a transmitter located in or on the housing and capable of generating acoustic waves and propagating said acoustic waves outward from said housing;

a receiver located in or on the housing and capable of receiving reflected acoustic waves;

a mixer located in or on said housing and capable of generating an electric signal representative of a function of said propagated acoustic waves and said received acoustic waves;

a transducer located in or on the housing capable generating sound waves representative of said electric signal; and a coupler positioned between said transducer and the turret capable of transmitting said sound waves to the turret bore of the turret.

22. A chestpiece for a stethoscope, comprising:

a turret having a first port and a second port and channel means connectable to said first port and said second port for channeling sound waves entering said first port through said turret and for channeling sound waves entering said second port through said turret;

an acoustic device connected to said turret and capable of directing sound waves into said first port of said turret; and an ultrasound bell connected to said turret and capable of directing sound waves into said second port of said turret, wherein said ultrasound bell includes a transmitter capable of generating ultrasound waves and propagating said ultrasound waves outward from said ultrasound bell and a receiver capable of receiving ultrasound waves that are representative of a modified version of said propagated ultrasound waves.

23. A chestpiece for a stethoscope, comprising:

a turret having a first port and a second port and channel means connectable to said first port and said second port for channeling sound waves entering said first port through said turret and for channeling sound waves entering said second port through said turret;

an acoustic device connected to said turret and capable of directing sound waves into said first port of said turret; and an ultrasound bell connected to said turret and capable of directing sound waves into said second port of said turret, wherein said ultrasound bell includes a transmitter capable of propagating ultrasound waves outward from said ultrasound bell and a receiver capable of receiving reflected ultrasound waves.

24. The chestpiece of claim 23, wherein said ultrasound bell includes a transducer capable of emitting sound waves, said receiver generates an electric signal representative of said received ultrasound waves, and said transducer is electrically connected to said receiver such that said transducer emits sound waves representative of said electric signal.

25. The chestpiece of claim 24, wherein said ultrasound bell includes coupling means for channeling said transducer emitted sound waves from said transducer into said second port of said turret.

26. The attachment of claim 1, wherein said at least one received acoustic wave includes at least one reflection of said at least one propagated acoustic wave.

27. The attachment of claim 1, wherein said at least one received acoustic wave differs in frequency from said at least one propagated acoutic wave.

28. The attachment of claim 1, wherein the turret includes an acoustic bell and said housing is attachable to the turret via connection to said acoustic bell.

29. The attachment of claim 12, wherein said at least one received acoustic wave includes at least one reflection of said at least one propagated acoustic wave.

30. The attachment of claim 12, wherein said at least one received acoustic wave differs in frequency from said at least one propagated acoustic wave.

* * * * *